United States Patent [19]

Denney et al.

[11] 4,111,657

[45] Sep. 5, 1978

[54] CREATININE ASSAY AND REAGENT SYSTEM

[75] Inventors: Jerry W. Denney, Carmel, Ind.; Robert L. Long, Spartanburg, S.C.

[73] Assignee: American Monitor Corporation, Indianapolis, Ind.

[21] Appl. No.: 761,239

[22] Filed: Jan. 21, 1977

[51] Int. Cl.$^2$ .................. C09K 3/00; G01N 21/02; G01N 33/16
[52] U.S. Cl. .................................. 23/230 B; 252/408
[58] Field of Search ................... 23/230 B; 252/408

[56] References Cited

U.S. PATENT DOCUMENTS

| | | | |
|---|---|---|---|
| 3,411,887 | 11/1968 | Ku | 23/230 B |
| 3,446,751 | 5/1969 | Weichselbaum | 23/230 B X |
| 3,705,013 | 12/1972 | Dewhurst | 23/230 B |
| 3,894,843 | 7/1975 | Jarvis | 23/230 B |

*Primary Examiner*—Joseph Scovronek
*Attorney, Agent, or Firm*—Robert A. Spray

[57] ABSTRACT

An alkaline picrate reagent system useful for the quantitation of creatinine in biological fluids. Interference from constituents normally found in serum or urine is eliminated by the use of dimethylsulfoxide with preferably an aralkane detergent in combination with a kinetic or reaction rate analysis mode. It obviates the need for any pretreatment of the sample, and avoids the need of other chemicals in the system which if allowed to contaminate glassware would have a deleterious effect on other analyses performed in the laboratory.

6 Claims, No Drawings

CREATININE ASSAY AND REAGENT SYSTEM

BACKGROUND OF INVENTION AND ITS SIGNIFICANCE

This invention relates to a reagent system and methodology for the measurement of creatinine in biological fluids such as serum or urine.

Vital Medical Significance of Creatinine Assays

Measurements of creatinine are most commonly performed to provide the medical analyst with an accurate assessment of renal function, as creatinine concentrations in serum usually are elevated in the course of pathological renal dysfunction. However, measurements of creatinine, in serum or urine, may also be used as indices in the diagnosis and treatment of other disorders, such as muscular dystrophy or hypothyroidism. Thus, the creatinine assay has been widely recognized as having vital medical significance since at least as early as 1886.[1]

Nature of Creatinine, and its Relation to Creatine Measurement

Although creatinine is primarily a waste product, and as such plays no important role in biochemical functions of the body, its chemical precursor, creatine, has a vital biochemical role; for creatine is a basic building block of creatine phosphate which is the primary form of energy storage in muscle.

The need for accurate creatinine measurements is evidenced by the fact that most if not all measurements of creatine depend upon its artificial conversion to creatinine and subsequent analysis of the creatinine. Usually in this type of procedure, preformed or native creatinine is measured in a sample, and then an aliquot is treated in such a manner that any creatine present is converted to creatinine; and then the total creatinine is measured. The difference in these two analyses thus represents the amount of creatine in the sample.

Vital Need for Close Accuracy of Creatinine Measurement

As normal individuals will possess approximately two to four times as much creatinine as they do creatine, and since the creatine measurement depends upon two measurements of creatinine, the accumulative error of small differences in the two analyses further points to the need for extremely accurate creatinine measurements, for illustratively, an error of only 10% in each of the creatinine measurements could produce a significantly large error of 90% in the creatine measurement.*

---

*Algebraic proof of accumulative error:

In the proof of a 90% accumulative error, the following assumptions are made:
1. True creatine concentration = A
2. True preformed creatinine concentration = B
3. True creatine = (Creatine converted to creatinine + preformed creatinine) − Preformed creatinine = (A+B)−B
4. True creatine concentration (A) is one-fourth the true preformed creatinine concentration (B) I.e., A = B/4 or 4A=B
5. In the two measurements of creatinine, a 10% error is made in each, and the direction of the error is different in each case.

Calculated Creatine = (Creatine changed to Creatinine + performed Creatinine) − preformed Creatinine Calculated Creatine $\stackrel{?}{=} .9(A+B)-1.1B$

---

*Algebraic proof of accumulative error:

$$\stackrel{?}{=} .9A+.9B-1.1B$$
$$\stackrel{?}{=} .9A-.2(B)$$

Substituting,

Calculated Creatine
$$\stackrel{?}{=} .9A-.2\times(4A)$$
$$\stackrel{?}{=} .9A-.8A$$
$$\stackrel{?}{=} .1A$$

But A≠.1A, a 90% error.
Similarly, if errors are reversed,
A≠1.9A, a 90% error.

---

Thus, small inaccuracies in the measurement of creatinine lead to seriously erroneous diagnoses and the attendant possibility (or likelihood) of costly and potentially harmful mistreatment of the patient.

Conversely, inaccurate measurements of creatinine may lead to a false impression of normalcy, and thus delay vitally-needed treatment of an existent pathology.

Prior Art, and its Disadvantages and Failures

The prior art has shown a long but ineffective struggle to fill a long-felt need of a means for providing a successful creatinine assay, and to overcome the lack of specificity inherent in the earliest procedures which had shown a color-developing reaction by which creatinine could be attempted to be quantitated.

That prior art dates clear back to the two fore-runners, in 1886 and 1904. That is, in 1886, Jaffé described the formation of a red color by reaction of creatinine with picrate in an alkaline solution;[2] and in 1904, Folin applied the Jaffé reaction to the quantitative determination of creatinine in urine.[3] (Since the time of Jaffé's work, alkaline picrate reagents used to measure creatinine have been generally described as Jaffé reagents and the reaction with creatinine described as the Jaffé reaction).

Although the Jaffé reaction achieves a measurable result, it has been known for many years that the Jaffé reaction has had a significant defect, particularly in that it lacks specificity in the measurement of creatinine in serum and urine. That is, such substances as ascorbic acid, pyruvic acid, acetone, glucose, protein, hydroquinone, rescorcinol glutathione, cystine, ergothionine, and many other substances found in blood serum or urine, interfere with the creatinine reaction or observation when the Jaffé reaction is used.[4] These interfering substances may be termed extraneous chromogens which, like creatinine, produce a chromophore or color in a Jaffé type reaction. The chromophore produced by extraneous chromogens is the primary cause of interference in the Jaffé reaction.

As a consequence of the recognition of the lack of specificity in Jaffé reaction, a number of early attempts were made to improve specificity by various types of pretreatment of the sample. These attempts include protein precipitation and removal by filtration, preliminary oxidation of interfering substances with iodine, ether extraction, adsorbtion of the creatinine onto aluminum silicate, and adsorbtion of creatinine onto strong cation exchange resins.[5]

However, pretreatment methods are time consuming, and have a further particular disadvantage in that they do not lend themselves to automation. In addition, in many cases the pretreatment may solve only part of the specificity problem, or indeed it even may worsen the specificity of the assay for creatinine.

As an example of a pretreatment attempt which fails to provide advantages of the present invention, protein removal is the most commonly performed preparative step used in the prior art pretreatment attempts. However, protein removal does not remove all interfering substances, for it does not remove ascorbic acid, some sulfhydryls, ketones, glucose, and other non-protein interferences which themselves cause specificity problems.[6] In addition, the protein-removal method has the operational disadvantages that care must be taken that complete recovery of creatinine is obtained in the filtrate, else the analysis will be in error.

Furthermore another disadvantage of pretreatment by protein removal is that whatever variation exists in protein content of the various sera assayed, and of the standards, causes variation in the color of the final reaction mixture in the pH sensitive Jaffé reaction, due to pH shifts in the filtrate.

Throughout the entire period of time from 1904 until 1965, the prior art attempted many modifications. The principle focus of these modifications was to attempt to increase the specificity of the Jaffé reaction by pretreatment of the samples with a diverse variety of materials or substances, such as kaolin and aluminum silicate.[7] But although these methods achieved a certain amount of success, they inherently suffer the drawbacks and disadvantages of being time-consuming, technically more complicated, and, most important, were not and are not today easily adaptable to automation. Many of the details of the attempted modifications, and of their difficulties and/or disadvantages, are set forth more fully in text references such as the text just cited,[8] which illustrate many prior art failures.

In order to improve specificity in the protein-free filtrate, Slot, in about 1965, suggested an extra-step process of acidification of the alkaline picrate filtrate mixture after color measurement, and again determining the red color.[9] However, Heinegard and Tiderström, in 1972, noted that the acidification step used by Slot did not correct for the color formed by some substances in serum such as glucose.[10]

In an attempt to correct this problem and also to eliminate the protein removal step, Heinegard and Tiderström employed an aralkane sulfate of sodium (sodium-dodecyl-sulfate) in combination with borate to improve specificity. These authors, incidentally, confirmed that the pH of the reaction was important in improving specificity for creatinine. However, although the Heinegard and Tiderström method had advantage over Slot's method, it still required the use of an acidification step in the process.

In about 1971, Cook suggested that creatinine could be assayed in the presence of protein, by making use of the kinetics of the color development in the Jaffé reaction for creatinine.[11] Larsen[12] and Lustergarten,[13] in 1972, published methods for creatinine assay based on rate of reaction or kinetic means.

Although the kinetic method represented a furtherance of the art in partially eliminating interference from extraneous chromogens in the Jaffé reaction, the kinetic approach represented a step backward in that a new source of interference from protein troubled the method. It was observed that protein altered the rate of the reaction of creatinine. Since kinetic methods quantitate creatinine by measuring rate of reaction, the kinetic method showed interference from protein.

The procedure of Larsen, recognizing this new mode of interference and the method's failure to eliminate this new protein effect, advocated the use of an empirically derived correction factor, in an attempt to overcome differences in the observed reaction rate due to protein. However, since biological material varies in protein content, and since it is often desirable to assay both urine and serum in the same automated procedure, thus requiring different correction factors, such attempted correction is at best bothersome and at worst inadequate.

Jarvis, in 1974, taught that the use of urea and sodium phosphate in combination with an aralkane sulfate detergent such as sodium dodecyl sulfate and borate could be used to "suppress" interfering chromogens and eliminate the use of a serum blank.[14] Although Jarvis taught that kinetic methods might be subject to interference by non-creatinine chromogens, the method of Jarvis itself has a disadvantage in that it shows interference from bilirubin when present in serum. An additional disadvantage of the Jarvis method is that the use of urea in the reagent introduces new problems not previously seen in the prior art, namely the urea causes the color which is formed by reaction of the Jaffé reagent with creatinine to be diminished and also unstable.

As a further disadvantage of the Jarvis method, its expressly specified use of urea may be potentially dangerous in the clinical laboratory, since urea itself is a commonly measured substance in blood and is used as is creatinine measurement, as a diagnostic indicator of kidney disease; for the amount of urea used in the Jarvis reagent is approximately 200 times that found in blood and the amount of urea used in each test is approximately 40,000 times that commonly added as a sample of blood. Consequently, laboratory glassware or instrumentation may be grossly contaminated with a very slight amount of the Jarvis reagent, leading to a possible mistaken assay for urea on a patient. Such contamination might at best cause delay and bother in a laboratory and at worst might cause a mistaken diagnosis or treatment to be made.

Further, in contrast to Jarvis who denounced kinetic assay methods, the present invention is advantageously used in kinetic assay.

THE PRESENT INVENTION

Achievements of the Present Invention Summarized

In contrast to the inadequacies of the prior art as indicated above, the concepts of the present invention advantageously achieve new reagents, and a new assay for the determination of creatinine in biological fluids which does not require the complicated and time-consuming pretreatment step of removal of proteins prior to the assay for creatinine.

Further, this invention provides and achieves, in a creatinine assay, an analytical procedure and reagent system which obviates the need for any sample pretreatment whatever.

Moreover, the concepts of this invention provide and achieve a stable reagent system and assay which overcome the effects of interfering substances commonly found in biological fluids, hence achieving greater specificity, without recourse to chemicals which, due to their presence in the reagent system, may seriously contaminate other chemical analyses being performed in the laboratory.

Also, the invention provides for the elimination of the disadvantageous effect of protein in prior art kinetic creatinine methods. As previously described, prior art kinetic methods were troubled by the effect of protein in modifying the rate of reaction of creatinine as compared to the rate of reaction in Jaffé reagent in the absence of protein. The concepts of the present invention achieve parity in reaction rate between creatinine assayed in serum and aqueous standards and between serum (which contains protein) and urine (which generally does not contain significant amounts of protein).

These and still further objects, features, advantages and achievements of the present invention will become apparent upon consideration of the following detailed disclosure of specific illustrative embodiments thereof.

Summary of the present Invention

The present invention utilizes an alkaline picrate solution to kinetically measure the amount of creatinine present in a sample of biological fluid. The interference normally encountered from proteins which are normally present in the sample is suppressed by the incorporation of dimethylsulfoxide in the test system.

(The particular nature or mechanism of the suppression is not clearly understood, even in the light of this invention which has discovered and achieved the suppression, although studies indicate that confirmational changes of substances, particularly proteins, may be the responsible mechanism of suppression involved. But the particulars or precise scientific explanation of the suppression, whether it be a suppression of the substances in the fluid or be of the effect of those substances, is not here asserted as a part of the invention.)

Preferably an aralkane sulfate type detergent, an agent which has been described in prior literature as aiding in the suppression of protein, is combined with the dimethylsulfoxide to further diminish the effects of the protein interference.

Although the present invention utilizes a kinetic reaction mode to measure creatinine, one skilled in the art may readily observe that the non-protein and non-creatinine interferences, which are fast reacting and are not measured in a kinetic procedure, may be eliminated by use of an identical reagent system and a serum blank mode in which non-creatine contributions to the final color developed are accounted for and thus are not considered in the calculation of creatinine.

Description of Specific Embodiments

The specific embodiments of the present invention detailed herein are provided to enable an analyst skilled in the art to clearly understand and produce reagents and an assay system according to the inventive concepts and achievements in the present invention.

Preparation of the reagents (a) Picrate reagent:

Approximately 4 and preferably about 4.2 or more grams of picric acid are added to 200 milliliters of dimethylsulfoxide and allowed to dissolve. To this mixture is added approximately 4.0 milliliters of an aralkane sulfate type detergent (e.g., a Gardinol type detergent such as "Teepol"[15] which is a mixture of sodium salts of sulfated fatty alcohols). The reagent is then mixed with distilled $H_2O$ and brought to a final volume of one liter. The reagent is stable indefinitely at room temperature when protected from light. (By the use of phrases such as "a sulfonated aralkane type" or an "aralkane sulfate type" detergent, it is meant to include either a mixture or a pure solution of sulfated fatty alcohols.)

(b) Alkaline reagent:

The alkaline reagent is prepared by dissolving approximately 12 grams of sodium hydroxide in one liter of distilled or purified water.

(c) Working alkaline picrate reagent:

The working alkaline picrate reagent is prepared by mixing equal parts of the picrate and alkaline reagent. This working reagent has demonstrated stability in excess of five days when stored at room temperature and protected from light.

Using the reagents of the present invention, and as described above, in the assay of creatinine in biological fluids, a sample to reagent ratio of about 1:40 to 1:20 is most commonly employed, and preferably a sample of 0.2 ml is mixed with 4.0 ml of the working alkaline picrate. As is common in creatinine measurement using picric acid,[16] the reaction is sensitive to temperature, and thus it is preferred that the reagent be incubated at a constant temperature prior to introduction of the sample.

The sample and reagent mixture is then introduced into a temperature-controlled spectrophotometer or colorimeter, and the increase in optical density with respect to time is measured at a wavelength between 480 and 530 nm. Preferably, a wavelength of 520 nm is used.

The creatinine concentration is then calculated by observing the rate of color developed for the unknown and comparing it to the rate of color developed by a known or standard concentration of creatinine. For ease, the following formula may be used:

$$\text{Concentration of unknown} = \frac{(\text{Rate of change of Optical Density})_{unknown}}{(\text{Rate of change of Optical Density})_{standard}} \times \text{Concentration of standard}$$

It should be noted that the reagent itself may tend to form a colored complex even in the absence of creatinine, said complex absorbing generally between 480 and 530 nm. Thus the reagent, especially when freshly prepared, will tend to have an observable rate of increase in color in and of itself. It is considered important thus to measure this blank reaction or "creep rate" of the reagents under the same conditions as the standards and unknowns are measured, and to subtract this rate from all standards and unknowns to adequately correct for this phenomenon. Most commonly found automated chemical analyzers used in clinical chemistry labs provide a readily available means for making this correction.

The reaction, or increase in color formed, has been found to be linear with respect to creatinine concentration when read between 15 seconds and 1 minute after introduction of sample and reagent. This particular system has been found to produce a linear response to at least 10 mg/dl of creatinine.

From the foregoing description, one skilled in the art is able to ascertain the essential characteristics of the present invention, and will readily perceive that minor modifications to the reagent system may be made and not depart from the inventive concepts set forth herein.

For example, the alkaline reagent is described as being prepared such that when the final working alkaline picrate reagent is prepared, the sodium hydroxide concentration will be approximately 6 gm/L. One may alter the sodium hydroxide concentration in the final reaction mixture from the broadly optional concentrations of about 2 gm/L to about 8 gm/L and not depart from the overall inventive concepts. It has been found that with the higher alkaline concentration the rate of the reaction is increased, but is linear for a shorter period of time. Thus, depending upon the particular application of the invention, one may alter hydroxide concentration within a fairly wide range to provide an optimal assay system, for his particular piece of instrumentation or application.

Further, the concentration of dimethylsulfoxide in the final reaction mixture may be as low as 5% (v/v), achieving a significant suppressive effect on the interference due to proteins, although up to approximately 10% (v/v) concentration of dimethylsulfoxide is preferably used in relatively high-protein solutions.

And although the present invention is described above in terms of its use in a kinetic mode of assay, it is equally utilizable in other modes (i.e. non rate measurements) such as in a serum blank mode in which two aliquots of sample are placed in contact with the reagent system for differing periods of time and the differences in optical density between the identically treated tubes are due to the reaction between creatinine and the alkaline picrate reagent.

Thus such modifications, and minor departures from the above example, are considered to be fairly and equitably within the scope of claims as set forth below.

CITATIONS OF REFERENCES

1. Jaffé, M., Ueber den Niederschlag, welchen Pikrinsaeure in normalem Harn erzeught und ueber eine neue Reaktion des Kreatinins, *Z. Physiol. Chem.*, 10:391-400, 1886, as cited in *Standard Methods of Clinical Chemistry*, Vol. 3, Seligson, D., editor, p. 111, Academic Press, New York and London, 1961
2. ibid.
3. Folin, O., Beitrag zur Chemie des Kreatinins und Kreatins im Harn, *Z. Physiol. Chem.*, 41:223-242 (1904), as cited in *Standard Methods of Clinical Chemistry*, ibid., p. 112
4. *Standard Methods of Clinical Chemistry*, ibid., p. 99
5. ibid., p. 99
6. ibid., p. 99
7. ibid., p. 99
8. ibid., p. 99-113
9. Slot, C., *Scand. J. Clin. Lab. Invest.*, 17:381 (1965)
10. Heinegard, D. & Tiderström, G., *Clin. Chem. Acta*, 43:305 (1973)
11. Cook, J., *Clin. Chem. Acta*, 32:485 (1971)
12. Larsen, K., *Clin. Chem. Acta*, 41:209 (1972)
13. Lustgarten, J. & Wenk, R., *Clin. Chem.*, 18:1419 (1972)
14. Jarvis, Alvar, U.S. Pat. No. 3,894,843 (1975)
15. *The Merck Index*, 8th ed., p. 482 (Merck & Co., 1968)
16. Lustgarten, J., supra, p. 1420

What is claimed is:

1. In a colorimetric or spectrophotometric assay for the quantitation of creatinine in biological fluids,
   in which a sample of the biological fluid, containing creatinine, is added to an alkaline picrate solution, the change in or the rate of change in optical density of the mixture being measured at a wavelength of between about 480 and 530 nm, and the creatinine content being then calculated by a comparison to the observed change or rate of change in optical density of a solution with a known concentration of creatinine;
   the improvement of adding dimethylsulfoxide to the alkaline picrate reagent, for the suppression of interference due to proteins in the biological fluid being assayed.
2. An assay as described in claim 1, wherein the concentration of dimethylsulfoxide in the final reaction mixture is approximately 10% (v/v).
3. An assay as described in claim 1, wherein the concentration of dimethylsulfoxide in the final reaction mixture is at least 5% (v/v).
4. An assay as described in claim 1, in which the alkaline picrate reagent contains sodium hydroxide in an amount such that the concentration of sodium hydroxide in the final reaction mixture is at least 2 gm/L.
5. An assay as described in claim 1, in which the alkaline picrate reagent contains sodium hydroxide in an amount such that the concentration of sodium hydroxide in the final reaction mixture is between 2 gm/L and 8 gm/L.
6. An assay as described in claim 1, in which a sulfonated aralkane type detergent is used as a supplement to the dimethylsulfoxide to provide the said suppression of interference.

* * * * *

Dedication 4,111,657.—*Jerry W. Denney*, Carmel, Ind., and *Robert L. Long*, Spartanburg, S.C. CREATININE ASSAY AND REAGENT SYSTEM. Patent dated Sept. 5, 1978. Dedication filed Feb. 25, 1982, by the assignee, *American Monitor Corp.*

Hereby dedicates to the Public the entire remaining term of said patent.
[*Official Gazette June 29, 1982.*]